(12) United States Patent
Young

(10) Patent No.: US 10,818,393 B2
(45) Date of Patent: Oct. 27, 2020

(54) SYSTEM AND METHOD FOR CLINICAL DECISION SUPPORT

(71) Applicant: General Electric Company, Schenectady, NY (US)

(72) Inventor: Brian Joseph Young, Wauwatosa, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 616 days.

(21) Appl. No.: 14/875,779

(22) Filed: Oct. 6, 2015

(65) Prior Publication Data

US 2017/0098047 A1 Apr. 6, 2017

(51) Int. Cl.
*G16H 10/60* (2018.01)
*G16H 50/20* (2018.01)
*G16H 50/70* (2018.01)

(52) U.S. Cl.
CPC ............ *G16H 50/20* (2018.01); *G16H 10/60* (2018.01); *G16H 50/70* (2018.01)

(58) Field of Classification Search
CPC .... A61B 5/7246; A61B 5/7271; G16H 10/60; G16H 50/70; G16H 50/20
USPC ........................................................ 705/2
See application file for complete search history.

(56) References Cited

U.S. PATENT DOCUMENTS

| | | | |
|---|---|---|---|
| 6,564,090 B2 | 5/2003 | Taha et al. | |
| 7,783,342 B2 | 8/2010 | Syeda-Mahmood et al. | |
| 8,951,193 B2 | 2/2015 | Ong et al. | |
| 2006/0111644 A1* | 5/2006 | Guttag | A61B 5/048 600/544 |
| 2006/0122525 A1* | 6/2006 | Shusterman | A61B 5/04007 600/513 |
| 2006/0135876 A1 | 6/2006 | Andresen et al. | |
| 2006/0200010 A1 | 9/2006 | Rosales et al. | |
| 2010/0004549 A1 | 1/2010 | Kohls et al. | |
| 2010/0228138 A1 | 9/2010 | Chen | |
| 2013/0012827 A1 | 1/2013 | Kurzweil et al. | |
| 2014/0107511 A1* | 4/2014 | Banet | G06Q 50/24 600/516 |

OTHER PUBLICATIONS

International Search Report and Written Opinion for Corresponding PCT application PCT/US2016/055158 dated Jan. 6, 2017; 8 pages.

(Continued)

*Primary Examiner* — Hiep V Nguyen
(74) *Attorney, Agent, or Firm* — Andrus Intellectual Property Law, LLP

(57) ABSTRACT

A system for clinical decision support includes a database of previously-recorded waveform data from comparator-patients and a comparator module. The comparator module receives physiological waveform data for a patient and identifies a pattern in the patient's physiological waveform data, wherein the pattern accounts for a morphology and a rhythm of the patient's physiological waveform. The comparator module then compares the patient's physiological waveform data to the previously-recorded waveform data using a pattern recognition algorithm to detect the pattern in the previously-recorded waveform data to identify one or more matches. The comparator module further generates a result set based on the one or more matches.

19 Claims, 6 Drawing Sheets

(56) References Cited

OTHER PUBLICATIONS

European Search Report dated Apr. 9, 2019.
W Baxt et al: "A neural network aid for the early diagnosis of cardiac ischemia patients presenting to the emergency department with chest pain", Annals of Emergency Medicine, vol. 40, No. 6, Dec. 1, 2002 (Dec. 1, 2002), pp. 575-583, XP055012444, ISSN: 0196-0644, DOI: 10.1067/mem.2002.129171 *First paragraph; p. 581* *table 1*.

* cited by examiner

SYSTEM AND METHOD FOR CLINICAL DECISION SUPPORT

BACKGROUND

Electrophysiological monitoring is a common way to assess the health of a patient and to diagnose and/or detect the presence of an adverse health condition. For example, an electrocardiograph (ECG) is a standard electrophysiological monitoring performed to assess cardiac health, and an electroencephalograph (EEG) is often performed in assessing brain health. Sometimes the results of electrophysiological monitoring produce results that indicate abnormalities; however, the abnormalities may not meet criteria for any identifiable condition. Such results are typically considered inconclusive or ambiguous. For example, many times ECG waveforms exhibit characteristics that divert from a normal, healthy ECG; however, the waveforms may not meet, or the clinician may not be able to identify within the ECG waveforms, any specified criteria for diagnosing a cardiac condition in those situations, a clinician may be unable to glean any useful information from the waveforms and any disregard the results of the physiological monitoring as inconclusive and as not providing any indication regarding patient health or diagnosis.

SUMMARY

The present disclosure includes a system and method for clinical decision support that overcomes the problems and challenges described above relating to inconclusive or ambiguous physiological waveforms. This summary is provided to introduce a selection of concepts that are further described below in the Detailed Description. This summary is not intended to identify key or essential features of the claimed subject matter, nor is it intended to be used as an aid in limiting the scope of the claimed subject matter.

In one embodiment, a system for clinical decision support includes a database of previously-recorded waveform data from comparator-patients and a comparator module. The comparator module receives physiological waveform data for a patient and identifies a pattern in the patient's physiological waveform data, wherein the pattern accounts for a morphology and a rhythm of the patient's physiological waveform. The comparator module then compares the patient's physiological waveform data to the previously-recorded waveform data using a pattern recognition algorithm to detect the pattern in the previously-recorded waveform data to identify one or more matches. The comparator module further generates a result set based on the one or more matches.

One embodiment of a method of clinical decision support includes the steps of acquiring a physiological waveform data for a patient and identifying a pattern in the patient's physiological waveform data, wherein the pattern accounts for a morphology and a rhythm of the patient's physiological waveform data. The method further includes accessing a database of previously-recorded waveform data from comparator-patients and comparing the patient's physiological waveform data to the previously-recorded waveform data using a pattern matching algorithm to detect the pattern in the previously-recorded waveform data to identify one or more matches, and then generating a result set based on the one or more matches.

In one embodiment, a non-transitory computer readable medium has computer-executable instructions stored thereon, wherein the instructions include the steps of acquiring a physiological waveform data for a patient; identifying a pattern in the patient's physiological waveform data, wherein the pattern accounts for a morphology and a cardiac rhythm of the patient's physiological waveform data; accessing a database of previously-recorded-waveform data from comparator-patients; comparing the patient's physiological waveform data to the previously-recorded waveform data using a pattern recognition algorithm to detect the pattern in the previously-recorded waveform data to identity one or more matches; and generating a result set based on the one or more matches.

Various other features, objects and advantages of the invention will be made apparent from the following description taken together with the drawings.

BRIEF DESCRIPTION OF THE DRAWINGS

The drawings illustrate the best mode presently contemplated of carrying out disclosure. In the drawings.

DETAILED DESCRIPTION

Figure 1:
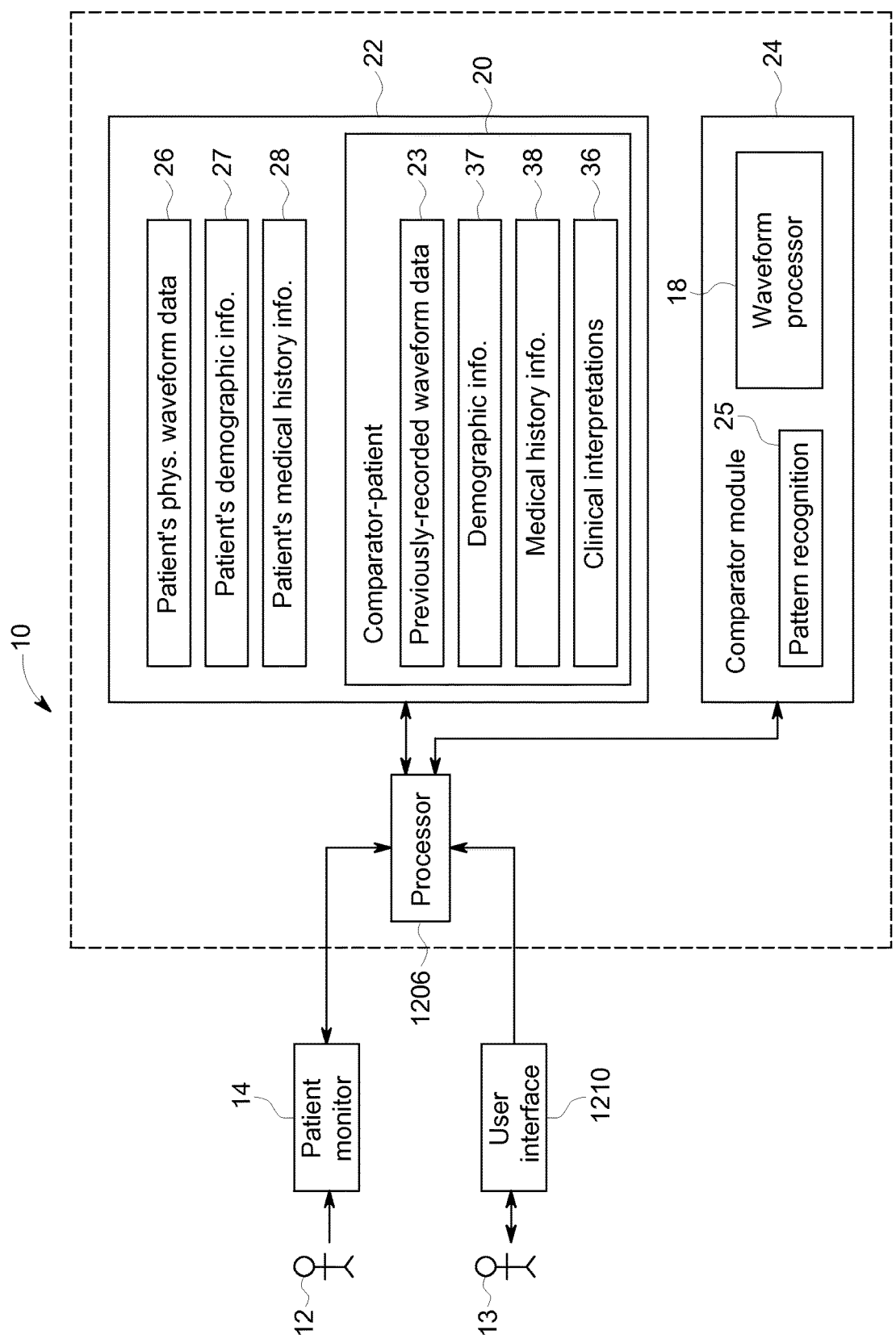
FIG. 1 depicts one embodiment of a system for clinical decision support.

FIG. 1 depicts one embodiment of a system 10 for clinical decision support. The system 10 and method 40 for clinical decision support disclosed herein overcomes the problems and challenges relating, to inconclusive or ambiguous physiological waveforms by taking advantage of existing, databases of clinically validated physiological waveforms or test cases involving a multitude of different patients, and leveraging the information learned in those cases in order to provide clinical interpretations, diagnoses, and/or clinical paths relevant to the physiological waveform data 26 for a current patient 12. More specifically, the present inventors have recognized that incidents of inconclusive or ambiguous physiological waveform results can be significantly decreased by comparing the patient's physiological waveform data 26 at issue to previously-recorded waveform data 23 from other comparable patients with similar waveform features, including similar waveform morphology and similar cardiac rhythms.

The patient's physiological waveform data 26, or a pattern therein, is compared to previously-recorded waveform data 23 from multiple comparator-patients 20 in order to identify one or more matches. For example, the comparison and match identification may be executed by utilizing a pattern recognition algorithm 25 to detect a pattern from the patient's physiological waveform data 26 in one or more waveforms in the previously-recorded waveform data 23. A result set is then generated based on the one or more matches. The result set includes the matching previously-recorded waveform data 23, which exhibit the same abnormal features or patterns as the patient's physiological waveform data. The result set may further include clinical interpretations 36 of the previously-recorded waveform data 23 of the matches, which may include such things as a diagnosis, a treatment plan, or a diagnostic or clinical path associated with the previously-recorded waveform data 23.

The present inventor has also recognized that an important feature and benefit of the system and method disclosed herein is that it may leverage and be integrated into existing management systems for physiological waveform data currently installed in hospitals and clinics. One exemplary such system is the MUSE system, which is an ECG management system produced by General Electric Company of Schenectady, N.Y. Furthermore, the present disclosure provides a method and system by which clinicians can leverage existing databases hosting vast amounts of previously-recorded physiological waveform data to generate and provide a wealth of information regarding the health implications of virtually any physiological waveform; which is information that is heretofore been unrecognized and unused.

The system 10 includes a database 22 of previously-recorded waveform data 23 from one or more comparator-patients 20. As described above, such database systems are known and available in the art, such as the MUSE system. The previously-recorded waveform data 23 may be acquired by any known patient monitoring device 14, such as any ECG monitoring device or EEG monitoring device. Additionally, the previously-recorded waveform data 23 may be in any of numerous forms. For example, in an embodiment related to ECG, the previously-recorded ECG waveform data may include various types of ECG tests or data forms. In one preferred embodiment, the database is primarily or completely comprised of ten second recordings of 12-lead resting ECGs. Such ECG recordings are standard in the art. Further, uniformity in lead placement and test conditions—such as recordings of 10 seconds in length, using a standard 12-lead placement, taken when the patient is at rest—may lead to relative uniformity in the data that lends itself to making comparisons. Additionally, the 12-lead ECG data may be derived from ECG data collected from a reduced set of ECG leads. Such systems and methods of deriving 12-lead ECGs from alternate electrode configurations are known in the art, and include, for example, the EASI system produced by Koninklijke Philips N.V. of Amsterdam, Netherlands. However, it is contemplated that databases comprising any other and/or varied forms of recorded ECG waveform data may be employed.

The database 22 may further include demographic information 37 for the comparator-patients 20, which may include, but is not limited to, information such as gender, ethnicity, ancestry, age, geographic or regional location, etc. Such demographic information 37 may be a useful tool in identifying matches, as it is well-known that certain health conditions may be more prevalent in individuals of a certain gender, ethnicity, ancestry, age, etc. The database may also include medical history information 38 for the comparator-patients, and especially medical history information having some relation to the abnormality in the relevant physiological waveform. Medical history information 38 may include, for example, any relevant health conditions or events that could relate in any way to the previously-recorded physiological waveform data, such as health conditions that may cause or be the result of a physiologic abnormality captured in the previously-recorded physiological waveform data. For example, in systems and methods implementing ECG data, medical history information 38 may include any history of cardiac conditions or ailments, high blood pressure, the patient's weight and/or body mass index, medications, etc.

The database 22 may further include clinical interpretations 36 of the previously-recorded physiological waveforms. Clinical interpretations 36 may include, for example, a diagnosis, a treatment plan, or clinical path, such as further diagnostic tests or procedures, relating to the previously recorded physiological waveform data.

A physiological waveform data is recorded for a patient 12 by the patient monitor 14. As explained above, the patient monitor 14 may be any device that detects and enables the recording of physiological waveforms from the patient, such as an ECG monitor or an EEG monitor. In one exemplary embodiment, the physiological waveform data recorded by the patient monitor 14 is awn second recording of a 12-lead resting ECG for the patient 12. The physiological waveform data for the patient 12 is then transferred via the processor 1206 to the database 22, which also houses the previously-recorded waveform data 23 from other comparator-patients 20.

A clinician 13 may access the patient's physiological waveform data via user interface 1210 which is communicatively connected to the processor 1206. The clinician 13 may review the patient's physiological waveform data 26 and make a determination regarding whether the physiological waveform data is normal, or whether abnormalities are present. The clinician 13 may further determine whether the abnormalities meet any known criteria for specific clinical conditions. The clinician 13 may enter clinical interpretations 36 indicating the abnormality and, if possible, indicating a diagnosis and/or a treatment plan. However, situations may arise where the clinician 13 recognizes an abnormality in the patient's physiological waveform data 26, however is unable to determine whether the abnormality meets any known criteria for any specific clinical condition, and thus the result is inconclusive or ambiguous. In such a situation, the clinician 13 may provide input via the user interface 1210 to instruct the processor 1206 to employ the comparator module 24 to determine whether any matches for the patient's physiological waveform data 26 exist in the database 22. Additionally, the clinician 13 may highlight particular channels and/or data sections within the patient's physiological waveform data which exhibit the abnormality. In other embodiments, the clinician 13 may provide a qualitative or quantitative description of the abnormality. Alternatively or additionally, the clinician 13 may engage a waveform processor 18 within the comparator module 24 to automatically detect abnormalities in the patient's waveform data 26—i.e., differences between the patient's physiological waveform data 26 and a normal physiological waveform—and thus to automatically to identify, or assist in the identification of the abnormal pattern in the patient's physiological waveform 26. For example, the pattern may be a description of the abnormality in the patient's waveform data 26, such as a description of one or more differences between the patient's waveform data 26 and a normal waveform. For example, in the context of ECG, the waveform processor 18 may be or may engage a computerized analysis program that provides ECG interpretation criteria for both rhythm and morphology, such as the Marquette 12SL product by General Electric Company of Schenectady, N.Y. This automatic identification of the abnormality and pattern may be executed automatically by the comparator module 24, or may be executed upon instruction by the clinician 13.

The comparator module 24 then operates to compare the physiological waveform data for the patient 12 to the previously-recorded waveform data 23. The purpose of the comparison is to identify one or more matches, where the previously-recorded waveform data 23 exhibits the same abnormal, or noted, waveform features or patterns. In one embodiment, the processor 1206 implements the comparator module 24, which is comprised of software code with executable instructions to compare the patient's physiological waveform data 26 to the previously-recorded waveform data 23 in the database to identify the matches, and generate the result set based thereon. For example, the comparator module 24 may employ a pattern recognition algorithm 25 to detect an identified pattern present the patient's physiological waveform data 26 in certain ones of the previously-recorded physiological waveform data 23 from the comparator-patients 20. Where the same pattern is present, the pattern recognition algorithm 25 identifies a match.

The identified pattern from the patient's physiological waveform data may be, for example, a difference in amplitude or duration of the waveform, or any portion thereof. In an embodiment involving ECG, the identified pattern from the patient's physiological waveform data accounts for an abnormality by describing, either qualitatively or quantitatively, how the PQRST waveform, or portion thereof, differs from a normal cardiac rhythm and/or from a normal PQRST morphology. For example, a pattern from the patient's physiological waveform data 26 may account for a morphology and a rhythm of the waveforms by including an amplitude and width of a wave portion, such as an amplitude and width of a P wave, or may provide an amplitude and duration of an interval, such as a PR interval, a QRS complex interval, a QT interval, an ST segment amplitude, etc. Alternatively or additionally, the pattern from the patient's physiological waveform data may account for and/or include qualitative descriptions of the waveform, such as, "short PR segment," "wide QRS," "long QT interval," "ST elevation," "coved type ST elevation," "saddle-shaped ST elevation," "notched T wave," "biphasic T wave," or similar. Additionally, the pattern may describe and account for the patient's waveform data 26 over several cardiac cycles, or heart beats, and thus may capture differences from one cycle to another or trends occurring over multiple cycles. Moreover, the pattern may account for abnormalities in the patient's waveform data 26 across multiple leads. The pattern from the patient's physiological waveform data may be identified by the clinician, who may input interpretations of the waveforms and/or make waveform measurements via the user interface 1210 interacting with the processor 1206. Alternatively or additionally, as described above, the pattern from the patient's physiological waveform data 26 may comprise information identified by a waveform processor 18 of the comparator module 24.

Figure 2:
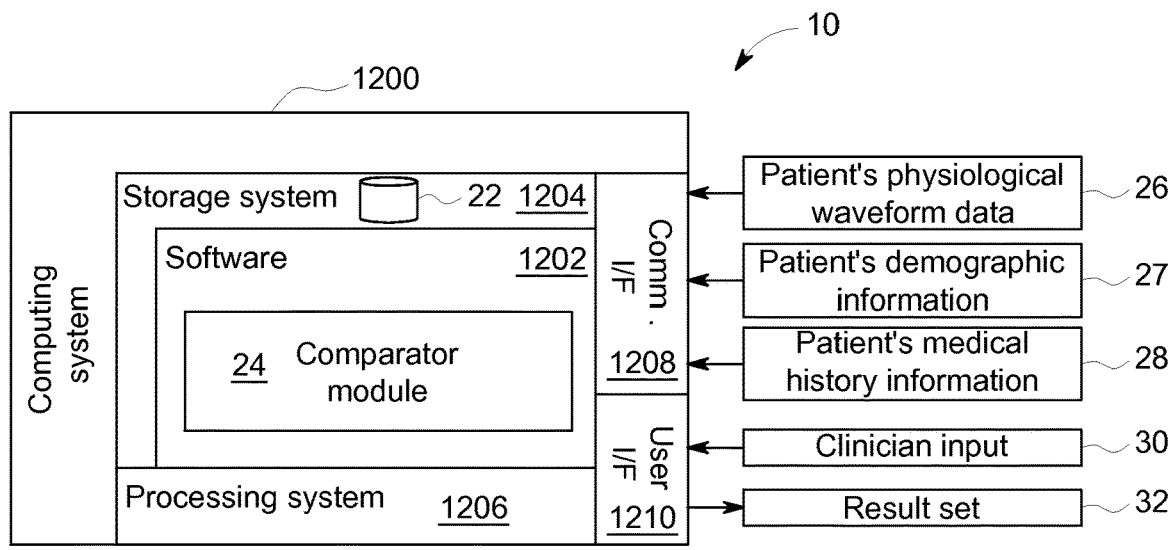
FIG. 2 depicts another embodiment of a system for clinical decision support.

FIG. 2 provides another system diagram of an exemplary embodiment of the system 10 for clinical decision support having a database 22 storing previously-recorded waveform data and a comparator module 24 executable to provide the comparisons and generate the result set as described herein. The system 10 is generally a computing system that includes a processing system 1206, storage system 1204, software 1202, communication interface 1208 and a user interface 1210, The processing system 1206 loads and executes software 1202 from the storage system 1204, including the comparator module 24, which is an application within the software 1202. The comparator module 24 includes computer-readable instructions that, when executed by the computing system 10 (including the processing, system 1206), the comparator module 24 directs the processing system 1206 to operate as described in herein in further detail, including to execute the steps of acquiring a physiological waveform data 26 for the patient 12, accessing database 22, comparing the patient's physiological waveform data 26 to the previously-recorded waveform data in the database 22 to identify one or more matches 33, and generating a result set 32 based on the one or more matches 33.

Although the computing system 10 as depicted in FIG. 2 includes one software 1202 encapsulating one comparator module 24, it should be understood that one or more software elements having one or more modules may provide the same operation. Similarly, while description as provided herein refers to a computing system 10 and a processing system 1206, it is to be recognized that implementations of such systems can be performed using one or more processors, which may be communicatively connected, and such implementations are considered to be within the scope of the description.

The processing system 1206 can comprise a microprocessor and other circuitry that retrieves and executes software 1202 from storage system 1204. Processing system 1206 can be implemented within a single processing device but can also be distributed across multiple processing devices or sub-systems that cooperate in existing program instructions. Examples of processing system 1206 include general purpose central processing units, applications specific processors, and logic devices, as well as any other type of processing device, combinations of processing devices, or variations thereof.

The storage system 1204, which includes the database 22, can comprise any storage media, or group of storage media, readable by processing system 1206, and capable of storing software 1202. The storage system 1204 can include volatile and non-volatile, removable and non-removable media implemented in any method or technology for storage of information, such as computer-readable instructions, data structures, program modules, or other data. Storage system 1204 can be implemented as a single storage device but may also be implemented across multiple storage devices or sub-systems. For example, the software 1202 may be stored on a separate storage device than the database 22. Storage system 1204 can further include additional elements, such a controller capable, of communicating with the processing system 1206. Likewise, database 22 can be stored, distributed, and/or implemented across one or more storage media or group of storage medias. Similarly, database 22 may encompass multiple different sub-databases at different storage locations and/or containing different information which may be stored in different formats. By way of example, the database 22 may encompass a MUSE ECG management system housing waveform data and an electronic medical record system housing demographic information.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processing system 1206, or may be distributed in one or more servers, which may be at multiple locations and networked, such as in cloud computing applications and systems. In some implementations, the store media can be a non-transitory storage media. In some implementations, at least a portion of the storage media may be transitory.

The user interface 1210 is configured to receive input 30 from a clinician, and to generate a result set 32 to the clinician. User interface 1210 can include a mouse, a keyboard, a voice input device, a touch input device for receiving, a gesture from a user, a motion input device for detecting non-touch gestures and other motions by a user, and other comparable input devices and associated processing elements capable of receiving user input, from a user, such as a clinician 13. Output devices such as a video display or graphical display can display an interface further associated with embodiments of the system and method as disclosed herein. Speakers, printers, haptic devices and other types of output devices may also be included in the user interface 1210.

As described in further detail herein, the system 10 receives the patient's physiological waveform data 26, and may also receive demographic information 27 and medical history information 28 for the patient. The patient's physiological waveform data 26 may be, for example, an output from a patient monitor, which may be in analog or digital form. In one example, the patient's physiological waveform data 26 may be in the form of a digital stored ECG record file in and ECG management system, such as the MUSE system, but may also be other types of files. Alternatively or additionally, the patient's physiological waveform data 26 may be in the form of an image file, such as a PDF file, which provides a graphic representation of an analog ECG signal. In still further embodiments, the patient's physiological waveform data 26 may be a streaming, analog input received in real time or near-real time by the system 10.

Figure 3:
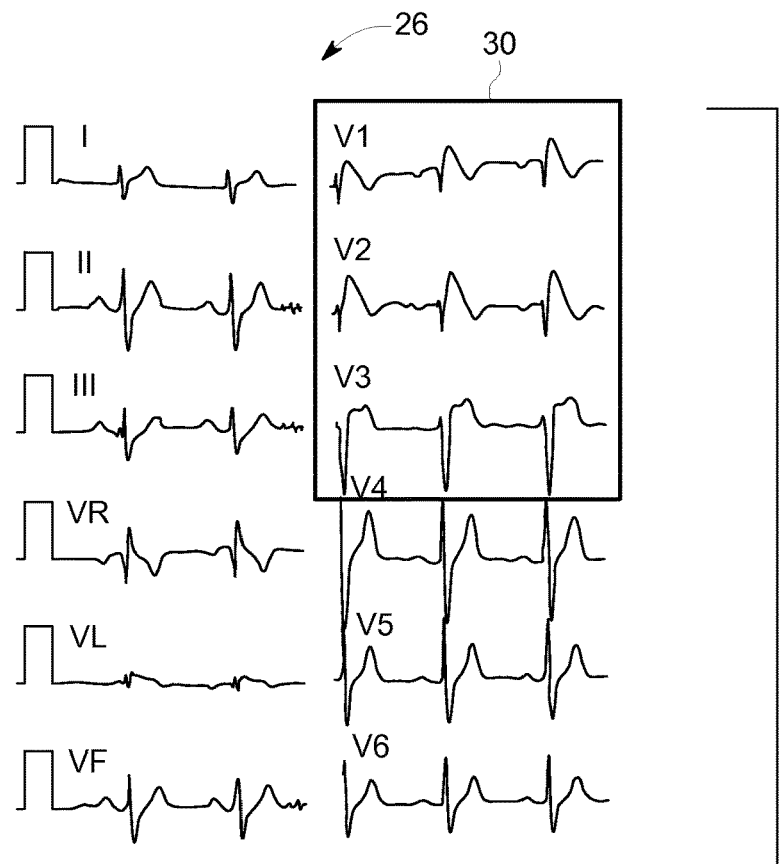
FIG. 3 depicts an example of a patient's physiological waveform data, demographic information, and medical history information.
Figure 4:
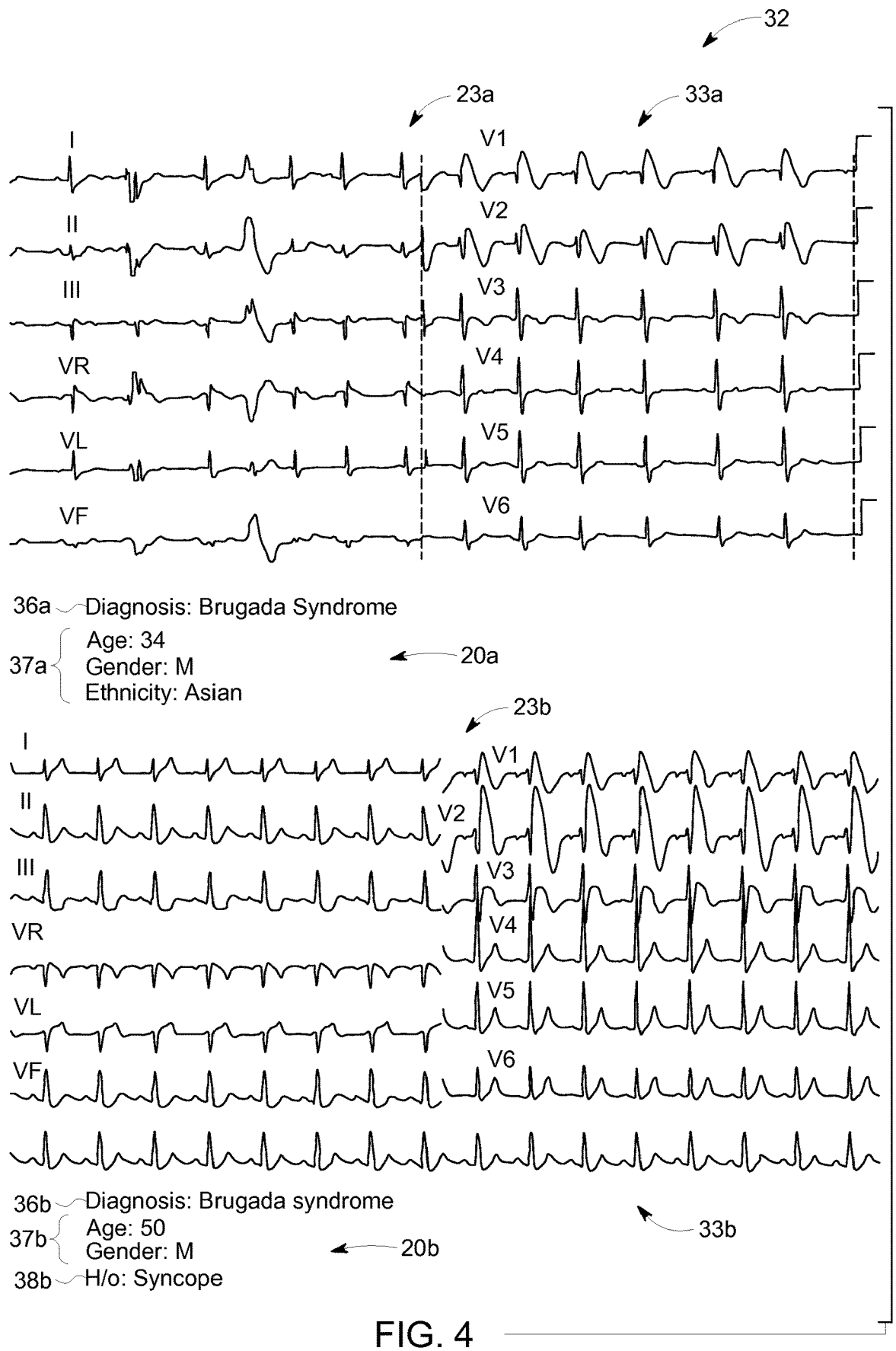
FIG. 4 depicts an exemplary result set providing matches to the patient's physiological waveform data.

The comparator module 24 generates a result set based on the one or matches identified from the comparison. FIGS. 3 and 4 depict an illustrative example. FIG. 3 depicts an exemplary recording of the patient's physiological waveform data 26. The exemplary patient's physiological waveform data 26 exhibits an abnormal pattern that is especially prevalent in the V1-V3 leads. In some embodiments, the clinician 13 may provide input 30 to indicate portions of the ECG recording exhibiting an abnormality to which they would like to find comparable waveform data, or matches. In the example of FIG. 3, the clinician 13 provides input 30 to identify a section of the patient's physiological waveform data exhibiting a pattern that deviates from a normal ECG and which, for purposes of this example, the clinician 13 is unable to associate with any specified criteria for diagnosing, a cardiac condition, and thus deems the ECG waveforms as ambiguous or inconclusive. In the example of FIG. 3, the input 30 identifies multiple cardiac cycles, or heartbeats, in channels V1-V3. In other examples, the clinician's input 30 could identify any other section or amount of data, such as one or multiple heartbeat waveforms in one or more channels, a segment or portion of a PQRST waveform in one or more channels, the entire waveforms in one or more channels, or the entirely of the patient's waveform data 26. In still other examples, the clinician may not provide any input 30 and the comparison could be conducted with respect to all 12 leads. Alternatively or additionally, a waveform processor 18 may identify the pattern of interest that contains an abnormality, and such waveform processor 18 may work in conjunction with the clinician's input 30 or in place of the clinician's input 30.

In still other embodiments, the physician could enter qualitative observations of the abnormal patterns seen in the waveforms. For example, the clinician 13 could provide input 30 identifying that they are searching for waveforms exhibiting similar "ST elevation" in channels V1-V3 to that in the patient's physiological waveform data 26. Further, input 30 could describe the qualitative aspects of the ST elevation, such as "saddle-shaped ST elevation," or could provide quantitative information about the elevation, such as an amplitude difference between the patient's physiological waveform data 26 and a normal ECG for each lead or the value of the area between the patient's physiological waveform data 26 and a normal ECG for each lead.

Additionally, the patient's demographic information 27 and medical history information 28 are also known by the system and used by the comparator module 24 to identify matches. For example, the demographic information identifies that the patient 12 is a middle-aged male individual of Asian ethnicity. Further, the medical history information 28 indicates that the patient has a history of syncope.

FIG. 4 depicts an exemplary result set 32 that may be generated by the comparator module 24 providing matches to the patient's physiological waveform data 26. The result set 32 includes a first match 33a having previously-recorded waveform data 23a from a first comparator-patient 20a, and a second match 33b having previously-recorded waveform data 23b from a second comparator-patient 20b. Both of the sets of previously-recorded waveform data 23a and 23b are ten second recordings of a 12-lead resting ECG. Both of the sets of previously-recorded waveform data 23a and 23b exhibit waveforms in the V1-V3 channels having a similar pattern to the patient's physiological waveform data 26—i.e. each set of previously-recorded waveform data 23a and 23b exhibits similar ST elevation in leads V1-V3 as is exhibited in the patient's physiological waveform data 26. Additionally, each match 33a and 33b has a corresponding diagnosis 36a and 36b indicating "Brugada Syndrome." Each match 33a and 33b also has demographic information 37a and 37b for each comparator-patient 20a and 20b, respectively.

Depending on the amount of previously-recorded waveform data 23 in the database 22 and the prevalence of the particular pattern exhibited in the patient's physiological waveform data 26, the result set 32 may comprise a large number of matches 33. It is contemplated that the result set 32 could be organized and presented to the clinician 13 in any number of ways, such as by providing the closest waveform match(es) 33 first. Alternatively or additionally, the comparator module 24 may further prioritize, sort, or narrow the list of matches based on one or more of the demographic information 37 and/or the medical history information 38 of the comparator-patients 20. In one embodiment, the comparator module 24 may be configured to identify those matches 33 that have a threshold level of similarity in demographic information, i.e., demographic matches, or have a threshold level of similarity in medical history information, i.e., medical history matches. Moreover, the comparator module 24 may be configured to weigh certain demographic factors heavier than others. The comparator module 24 may further be configured to identify patterns in demographic and/or medical history information amongst the matches to identify trends therein, and may weigh the identified trending demographic or medical history information more heavily in the comparison with the patient's demographic information 27 and/or medical history information 28.

Thus, in the context of FIGS. 3 and 4, the comparator module 24 may compare the patient's demographic information 27, including the patient's age, gender, and ethnicity, to the demographic information 37a and 37b of the two comparator-patients 20a and 20b. Both the matches 33a and 33b have certain demographic information in common with the patient's demographic information 27. Like the current patient 12, the comparator-patients 20a and 20b are both middle-aged males. Further, comparator-patient 20a is of the same ethnicity as the current patient. Likewise, the comparator module 24 may also compare the patient's medical history information 28 to the medical history information available for the matches 33a and 33b. In the example of FIG. 4, medical history information 38b is only available for comparator-patient 20b, which in the exemplary embodiment is a medical history match with the patient's medical history 28 because both the comparator-patient 20b and the current patient 12 have a history of syncope. The result set 32 also provides clinical interpretations 36a and 36b of each of the previously-recorded waveform data sets 23a and 23b, respectively. Both of the clinical interpretations 36a and 36b indicate a diagnosis of Brugada syndrome. All of this information may be provided to the clinician in the result set 32, and may prove useful to the clinician 13 in assessing the significance of the patient's physiological waveform data 26.

In another embodiment, the patient's demographic information 27 and medical history information 28 may be used to create a narrowed set of previously-recorded waveform data 23 from the larger available set in the database 22. For example, the clinician could presort the data so that the comparator module 24 only compared the patient's physiological waveform data 26 to previously recorded waveform data 23 from comparator-patients having a certain medical history, demographic, etc. Thus, the clinician 13 could select one or more criterion upon which the set of previously recorded waveform data would be narrowed, and then the patient's physiological waveform data 26 can be compared to the narrow set of previously-recorded waveform data elements 23. This could be especially useful, for example, if a clinician 13 wanted to examine the significance of a particular waveform pattern for patients having, a particular medical condition, patients in a certain risk group, patients of a particular demographic, patients on a particular medication, etc.

In still other embodiments, the comparator module 24 could prioritize or filter the matches 33 based on other factors, such as the amount of clinical interpretation information 36, medical history information 38, or demographic information 37 associated therewith, or the credibility of that information. For example, the credibility of the clinical interpretations 36 could be related to the seniority or sophistication of the clinician 13 that provided the clinical interpretations 36 of the previously-recorded waveform data 23. For example, each clinician 13 could be given a score based on their seniority, their specialty, their accolades, etc., and that score can be used as a credibility indicator. Alternatively or additionally, other factors may play into the sorting or filtering of the result set 32, such as the quality or clarity of the data (e.g., noise content), the date the data was taken, the location that the data was taken, the format of the data, etc.

Figure 5:
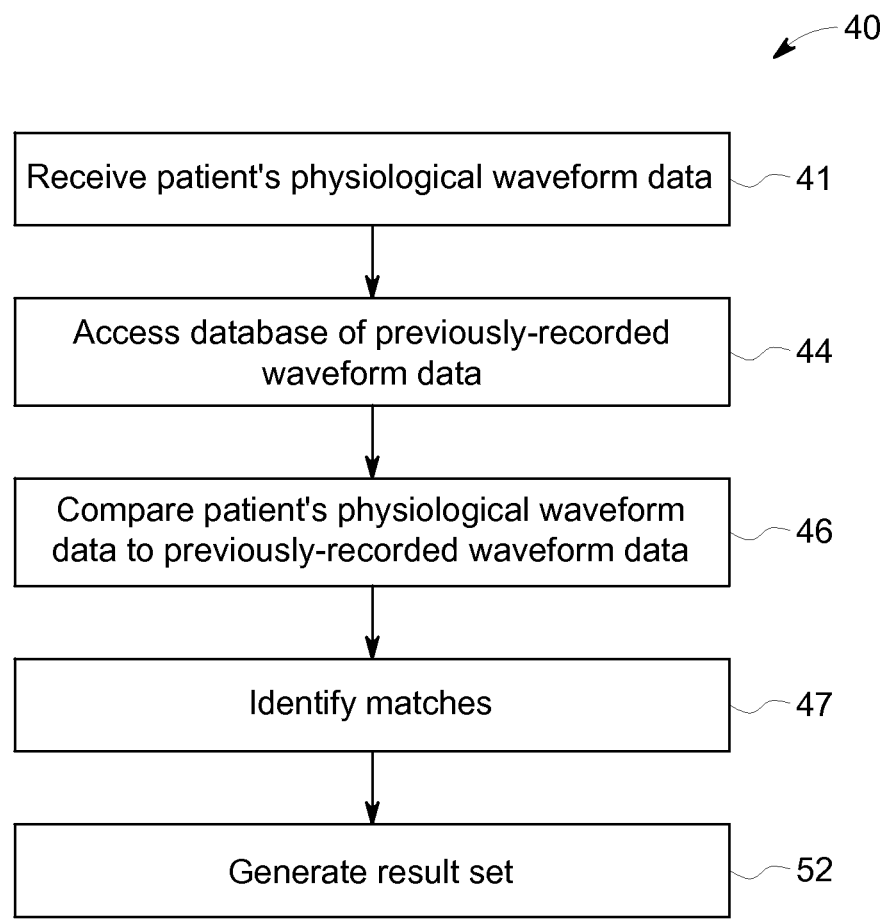
FIG. 5 depicts an embodiment of a method of clinical decision support.

FIG. 5 depicts one embodiment of a method 40 of clinical decision support. At step 41, a patient's physiological waveform data is received. The system then accesses a database of previously-recorded waveform data at step 44. At step 46, the system compares the patient's physiological waveform data to the previously-recorded waveform data. Matches are identified at step 47, and the result set is generated at step 52.

Figure 6:
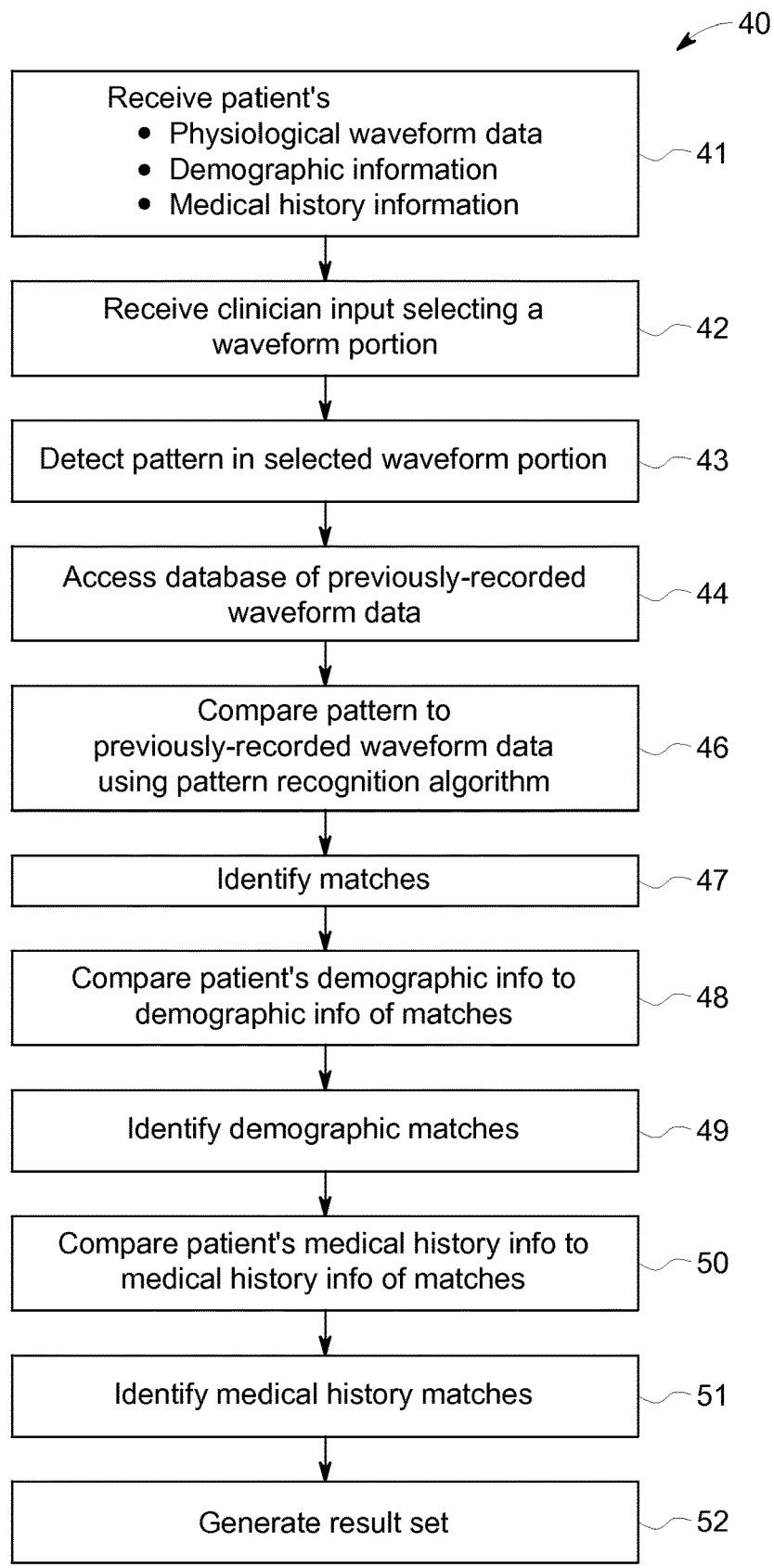
FIG. 6 depicts another embodiment of a method of clinical decision support.

FIG. 6 depicts another embodiment of a method 40 of clinical decision support. At step 41, the patient's physiological waveform data is received, along with the patient's demographic information and medical history information. Clinician input is received at step 42 selecting a waveform portion for further analysis and matching. At step 43, a pattern is detected in the selected waveform portion. A database of previously-recorded waveform data is then accessed at step 44. At step 46, a pattern recognition algorithm is used to compare the pattern in the selected waveform portion to the previously-recorded waveform data. At step 47, matches are identified therefrom. The matches are then filtered based on the patient's demographic and medical history information. Specifically, at step 48, the patient's demographic information is compared to the demographic information of the matches, and demographic matches are then identified at step 49. Likewise, at step 50, the patient's medical history information is compared to the medical history information of the matches, and medical history matches are identified at step 51. The result set is then generated at step 52 based on the medical history matches and/or the demographic matches. As is discussed above, the medical history and/or demographic information elements may be given various weights, and the result set may be sorted or prioritized such that the matches with the highest weighted score are presented at the top of the result set.

Figure 7:
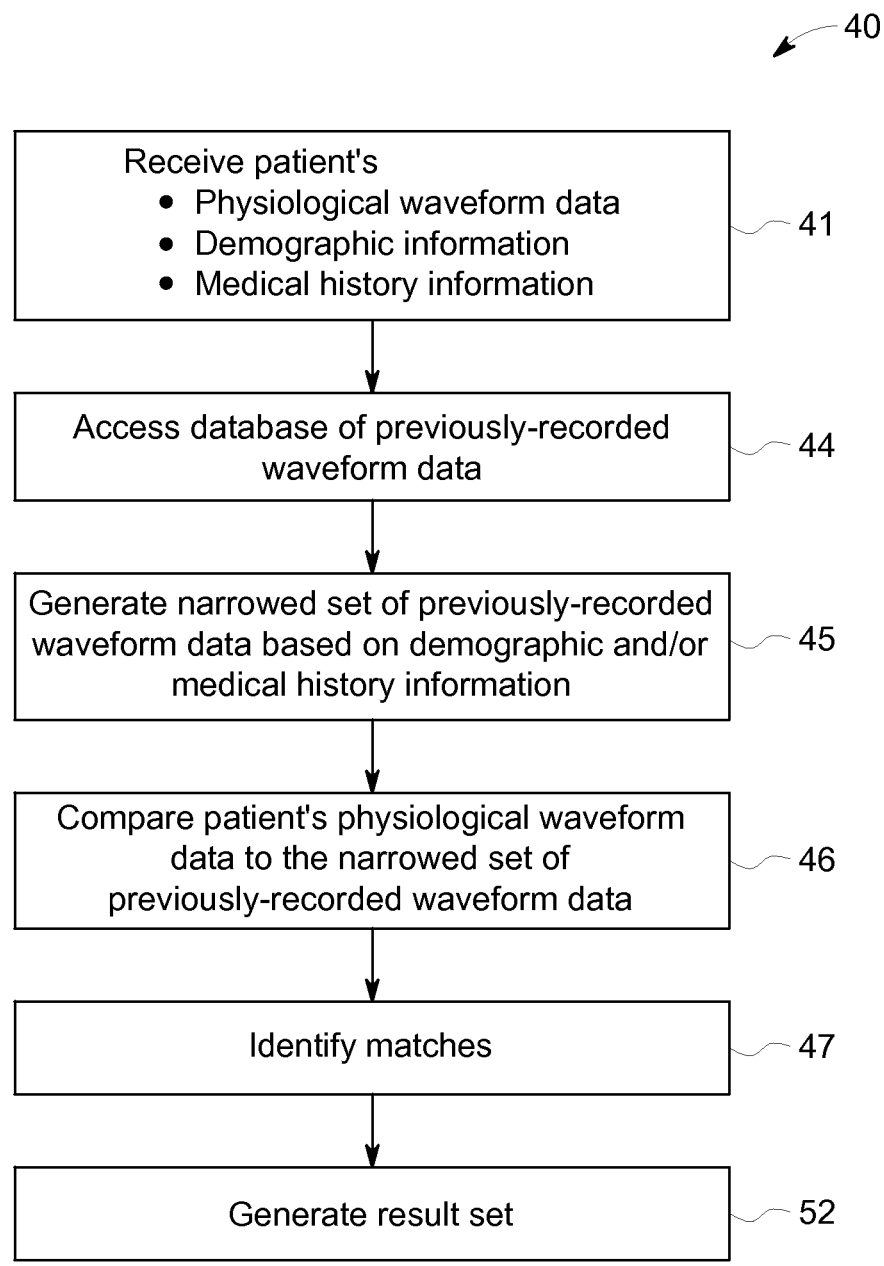
FIG. 7 depicts another embodiment of a method of clinical decision support.

FIG. 7 provides another embodiment of a method 40 of clinical decision support. At step 41, the patient's physiological waveform data is received, along with the demographic information and medical history information for the patient. The system then accesses the database of previously-recorded waveform data at step 44. At step 45, a narrowed set of the previously-recorded waveform data is generated based on the demographic and/or medical history information for the patient. The patient's physiological waveform data is then compared to the narrowed set of previously-recorded waveform data at step 46. Matches are identified at step 47, and a result set is generated at step 52.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system for clinical decision support, the system comprising:
   a database of previously-recorded electrocardiogram (ECG) waveform data from comparator-patients;
   a comparator module executable on a processor to:
   receive multi-lead ECG waveform data for a patient;
   identify an abnormality in the patient's ECG waveform data and then detect an abnormal pattern that accounts for multiple cardiac cycles in one or more leads in the patient's ECG waveform data, wherein the abnormal pattern accounts for a morphology and a rhythm related to the abnormality in the patient's ECG waveform data;
   using a pattern recognition algorithm, compare the patient's ECG waveform data to the previously-recorded ECG waveform data from comparator-patients in the database to detect the abnormal pattern in the previously-recorded ECG waveform data and to identify one or more matches in the previously-recorded ECG waveform data from the comparator-patients; and
   generate a result set based on the one or more matches, wherein the result set includes information from comparator-patients relevant to the abnormal pattern.

2. The system of claim 1, wherein the abnormal pattern accounts for multiple leads in the patient's ECG waveform data.

3. The system of claim 1, wherein the patient's multi-lead ECG waveform data is a 12-lead resting ECG.

4. The system of claim 1, wherein the comparator module automatically detects the abnormal pattern in the patient's ECG waveform data by identifying the abnormality, and then defines the abnormal pattern based on the abnormality.

5. The system of claim 1, wherein the database further includes clinical interpretations of each previously-recorded waveform data; and
wherein the result set includes the clinical interpretations of the previously-recorded waveform data of the matches.

6. The system of claim 5, wherein the clinical interpretations include at least one of a diagnosis and a treatment plan; and
wherein the result set includes the diagnosis or the treatment plan associated with the matches.

7. The system of claim 5, wherein the database further includes demographic information of each of the comparator-patients.

8. The system of claim 7, wherein the comparator module is further executable to:
receive demographic information for the patient;
compare the patient's demographic information to the demographic information of each of the matches to identify demographic matches; and
generate the result set further based on the demographic matches.

9. The system of claim 7, wherein the comparator module is further executable to:
receive demographic information for the patient;
generate a narrowed set of previously-recorded waveform data based on the patient's demographic information; and
compare the patient's ECG waveform data to the narrowed set of previously-recorded waveform data to identify the one or more matches.

10. The system of claim 5, wherein the database further includes medical history information of each of the comparator-patients.

11. The system of claim 10, wherein the comparator module is further executable to:
receive medical history information for the patient;
compare the patient's medical history information to the medical history information of each of the matches to identify medical history matches; and
generate the result set further based on the medical history matches.

12. The system of claim 10, wherein the comparator module is further executable to:
receive medical history information for the patient;
generate a narrowed set of previously-recorded waveform data based on the medical history information for the patient; and
compare the patient's ECG waveform data to the narrowed set of previously-recorded waveform data to identify the one or more matches.

13. A method of clinical decision support, the method comprising:
receiving at a processor multi-lead ECG waveform data for a patient;
detecting an abnormal pattern that accounts for multiple cardiac cycles in one or more leads in the patient's ECG waveform data, wherein the abnormal pattern accounts for a morphology and a rhythm related to an abnormality in the patient's ECG waveform data;
accessing with the processor a database of previously-recorded waveform data from comparator-patients;
using a pattern recognition algorithm, comparing the patient's ECG waveform data to the previously-recorded ECG waveform data from comparator-patients in the database to detect the abnormal pattern in the previously-recorded ECG waveform data and identifying one or more matches in the previously-recorded waveform data from the comparator-patients; and
generating with the processor a result set based on the one or more matches, wherein the result set includes information from the comparator-patients relevant to the abnormal pattern.

14. The method of claim 13, wherein the step of detecting the abnormal pattern in the patient's ECG waveform data includes receiving input from a clinician selecting a portion of the ECG waveform data.

15. The method of claim 13, wherein the step of detecting the abnormal pattern in the patient's ECG waveform data includes automatically identifying an abnormality in the patient's ECG waveform data.

16. The method of claim 15, further comprising:
receiving at least one of a demographic information and a medical history information for the patient; and
generating a narrowed set of previously-recorded waveform data based on patient's demographic information or medical history information.

17. The method of claim 13, wherein the database further includes clinical interpretations of the previously-recorded waveform data, demographic information of the comparator-patients, and/or medical history information for the comparator-patients, and wherein the result set includes the clinical interpretations of the previously-recorded waveform data of the matches.

18. The method of claim 17, further comprising:
receiving at least one of demographic information and medical history information for the patient;
comparing with the processor at least one of the patient's demographic information to the demographic information of each of the matches to identify demographic matches, and the patient's medical history information to the medical history information of each of the matches to identify medical history matches; and
generating with the processor the result set further based on at least one of the demographic matches and the medical history matches.

19. A non-transitory computer readable medium having computer-executable instructions stored thereon, wherein the instructions include the steps comprising:
acquiring a multi-lead ECG waveform data for a patient;
identifying an abnormal pattern that accounts for multiple cardiac cycles in one or more leads in the patient's ECG waveform data, wherein the abnormal pattern accounts for a morphology and a cardiac rhythm related to an abnormality in the patient's ECG waveform data;
accessing a database of previously-recorded waveform data from comparator-patients;
using a pattern recognition algorithm, comparing the patient's ECG waveform data to the previously-recorded ECG waveform data from comparator-patients in the database to detect the abnormal pattern in the previously-recorded ECG waveform data and identifying one or more matches in the previously-recorded waveform data from comparator-patients; and generating a result set based on the one or more matches, wherein the result set includes information from the comparator-patients relevant to the abnormal pattern.

\* \* \* \* \*